United States Statutory Invention Registration [19]

[11] Reg. Number: H619

McDaniel, Jr. et al. [43] Published: Apr. 4, 1989

[54] PREPARATION OF ALKYL GLYCOSIDES

[75] Inventors: Robert S. McDaniel, Jr., Decatur; Leonard F. Vanderburgh, Bethany; Stephen J. Sommer, Decatur, all of Ill.

[73] Assignee: A. E. Staley Manufacturing Company, Decatur, Ill.

[21] Appl. No.: 573,905

[22] Filed: Jan. 25, 1984

[51] Int. Cl.[4] ..... C07G 3/00; C07H 15/00; C07H 17/00

[52] U.S. Cl. ..... 536/18.6; 536/18.5

[58] Field of Search ..... 536/18.6, 18.5, 120, 536/124, 127

[56] References Cited

U.S. PATENT DOCUMENTS

| | | | |
|---|---|---|---|
| 2,276,621 | 3/1942 | Langois | 536/18.6 |
| 2,390,507 | 12/1945 | Cantor | 536/18.6 |
| 2,853,485 | 9/1958 | Werner et al. | 536/119 |
| 3,219,656 | 11/1965 | Boettner | 536/18.6 |
| 3,598,865 | 8/1971 | Lew | 536/18.6 |
| 3,839,318 | 10/1974 | Mansfield | 536/18.6 |

*Primary Examiner*—John F. Terapane
*Assistant Examiner*—Susan Wolffe
*Attorney, Agent, or Firm*—Philip L. Bateman

[57] ABSTRACT

Medium and long-chain alkyl glycosides are prepared by reacting a saccharide and a monohydric alcohol in the presence of at least 1 mole N-methyl-2-pyrrolidone per mole saccharide unit. The saccharide is selected from the group consisting of unsubstituted saccharides, short-chain alkyl glycosides, and mixtures thereof. The monohydric alcohol is selected from the group consisting of medium-chain alcohols, long-chain alcohols, and mixtures thereof. The reaction is conducted at a temperature of about 80° to 140° C.

11 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PREPARATION OF ALKYL GLYCOSIDES

FIELD OF THE INVENTION

This invention relates to alkyl glycosides. More particularly, this invention relates to a process for preparing medium and long-chain alkyl glycosides.

BACKGROUND OF THE INVENTION

A. Saccharides and Glycosides in General

Monosaccharides are polyhydroxy aldehydes and polyhydroxy ketones which, when unsubstituted,. have the chemical formula $C_nH_{2n}O_n$. Monosaccharides can join together, with the loss of water, to form chains of varying lengths. The length of a saccharide chain is commonly described either by adding a descriptive prefix to its name or by stating the chain's "degree of polymerization" (abbreviated to "D.P."). For example, glucose (also known as dextrose) is a monosaccharide having a D.P. of one; sucrose and maltose are disaccharides having a D.P. of two; and starch and cellulose are polysaccharides having a D.P. of 1000 or more. The term "saccharide" encompasses unsubstituted and substituted molecules of any chain length.

Glycosides are substituted saccharides in which the substituent group is normally attached, through an oxygen, to the aldehyde or ketone carbon. Accordingly, most glycosides are considered acetals. As with the term "saccharide", the term "glycoside" defines neither the number nor the identity of the saccharide units in the molecule. To describe the number of saccharide units, the same methods are used as outlined above. To describe the identity of the saccharide units, it is common to modify the name of the saccharide unit by adding the ending "-side". For example, a glucoside is a glycoside having one or more glucose units and a fructoside is a glycoside having one or more fructose units. Accordingly, the compound having the following chemical formula is a butyl glucoside of D.P. 2.

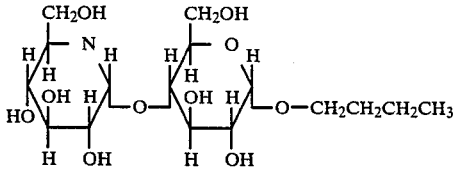

Glycosides having alkyl substituent groups are an especially useful class of compounds. Short-chain (1 to 3 carbon atoms) alkyl glycosides are commonly used as intermediates in preparing polyurethane foams, medium-chain (4 to 7 carbon atoms) alkyl glycosides, and long-chain (8 to 25 carbon atoms) alkyl glycosides. Medium-chain alkyl glycosides are used primarily as intermediates in preparing long-chain alkyl glycosides. Long-chain alkyl glycosides are known to be surface-active due to the hydrophilicity of their saccharide portions and the lipophilicity of their long-chain alkyl portions. Therefore, it is not surprising that long-chain alkyl glycosides have often been employed as detergents, emulsifiers, wetting agents, lubricants, etc.

B. Preparation of Glycosides

Commercially, alkyl glycosides are most often derived from crystalline glucose which is, in turn, most often derived from starch. The conversion of starch to a medium-chain alkyl glucoside (e.g. butyl glucoside) or to a long-chain alkyl glucoside (e.g. dodecyl glucoside) commonly requires, respectively, five or six steps:

(1) Pasting the starch to convert it from its granular and unreactive form into a reactive solution;

(2) Hydrolyzing the starch in the presence of acid and/or enzymes to convert it to glucose;

(3) Crystallizing the glucose;

(4) Reacting the crystalline glucose with methanol to produce methyl glucoside;

(5) Reacting the methyl glucoside with butanol to produce butyl glucoside; and (6) Reacting the butyl glucoside with dodecanol to produce dodecyl glucoside.

The plurality of steps is generally recognized as necessary because the more hydrophilic saccharides (e.g.-starch, glucose, and methyl glucoside) are immiscible, in varying degrees, with the lipophilic medium and long-chain alcohols. Because of the immiscibility and the resulting mass transfer limitations on the reaction, the rate of the reaction is prohibitively slow. Furthermore, it is believed that the competing reaction of saccharide polymerization predominates if the saccharides are in a liquid or aqueous state in which the saccharide molecules can align themselves sufficiently to polymerize. Accordingly, it is common practice to form chemical intermediates which are miscible with the chosen medium or long-chain alcohol. After the miscible intermediate is formed, the resulting liquid phase reaction proceeds relatively rapidly. Ever since the utility of medium and long-chain alkyl glycosides was discovered and the above five and six-step procedures employed to produce them, a major goal in the art has been to reduce the number of steps in the procedure.

For example, Langlois, U.S. Pat. No. 2,276,621, issued Mar. 17, 1942, discloses a process for converting starch directly to methyl glucoside thereby, in effect, combining the first four of the above-mentioned steps into one. Cantor, U.S. Pat. No. 2,390,507, issued Dec. 11, 1945, discloses a process for converting starch to butyl glucoside directly. Neither Langlois nor Cantor suggests the direct conversion of unsubstituted saccharides or short-chain alkyl glycosides to long-chain alkyl glycosides.

Boettner, U.S. Pat. No. 3,219,656, issued Nov. 23, 1965, discloses a process for converting unsubstituted saccharides to long-chain alkyl glycosides via the methyl glycoside and butyl glycoside intermediates, but without a separate isolation of the methyl glycoside or the butyl glycoside. The process employs an anhydrous macroreticular-structured sulfonic acid type cation exchange resin. Boettner further discloses that dimethylformamide and dimethylsulfoxide can be employed in the process to give partial solubility to the saccharide and the long-chain alcohol.

Lew, U.S. Pat. No. 3,598,865, issued Aug. 10, 1971, discloses a process for reacting unsubstituted saccharides and long-chain alcohols in the presence of a "latent solvent" to form long-chain alkyl glycosides. The "latent solvent" is a primary or secondary alcohol having from 3 to 5 carbon atoms, such as butanol. The role of the "latent solvent" in this process is to react with the saccharide to produce an intermediate alkyl glycoside which is miscible and reactive with the long-chain alcohol. Lew recognizes that the "latent solvent" is, in reality, a reactant. At column 2, lines 11 through 12, he states "The term 'latent solvent' denotes a medium which is actually not a solvent for the system in question . . . " Lew, U.S. Pat. No. 3,707,535, issued Dec. 26, 1972, and Lew, U.S. Pat. No. 3,772,269, issued Nov. 13, 1973, are similar except that different compounds are employed to produce the intermediate (aliphatic ether-alcohols in '535 and alkylene glycols in '269).

There are several disadvantages associated with processes such as Boettner and Lew in which intermediate reactants, e.g. butanol, and intermediate products, e.g. butyl glucoside, are employed, but the major disadvantage is the need to remove the intermediates from the final product. The intermediate products are especially difficult to separate from the final products because of their similarities in boiling points.

Mansfield, U.S. Pat. No. 3,839,318, issued Oct. 1, 1974, discloses a process for directly reacting unsubstituted saccharides and long-chain alcohols to form long-chain alkyl glycosides. To achieve the direct reaction, the Mansfield process is operated at conditions carefully chosen to avoid the competing saccharide polymerization reaction. For example, the molar ratio of alcohol to saccharide is greater than a minimum which varies with the chain length of the alcohol and the by-product water is removed as soon as it appears. In addition, although Mansfield does not disclose it and may not have recognized its importance, the saccharide is in its crystalline form. While these process conditions minimize the rate of the saccharide-polymerization reaction, they do not markedly increase the rate of the desired saccharide-alcohol reaction. Accordingly, reaction times for the Mansfield process are excessively long, especially when the longer chain alcohols are employed. Amsudio, European patent application Publication No. 0077167, published Apr. 20, 1983, discloses a process similar to Mansfield with the addition of an acid-reducing agent, such as hypophosphorus acid, to minimize color deterioration.

VanderBurgh, European Patent Application Publication No. 0092355, published Oct. 26, 1983, discloses a process for preparing long-chain alkyl glycosides by reacting saccharides and lipophilic alcohols in the presence of a surfactant additive represented by the structural formula $RO(G)_n$ where "R" represents a lipophilic group having at least 8 carbon atoms, "O" represents an oxygen atom, "G" represents a saccharide unit, and "n" represents a number having a value of at least 1. VanderBurgh states that the surfactant additive renders the saccharide and the lipophilic alcohol sufficiently compatible with one another to permit the desired reaction to occur.

C. N-Methyl-2-Pyrrolidone

N-methyl-2-pyrrolidone,

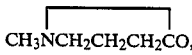

$CH_3NCH_2CH_2CH_2CO$, is a colorless liquid having a melting point of −24° C. and a boiling point of 202° C. It is used as a reaction solvent, a catalyst, a polymer solvent, an ingredient in coatings, and as an extractive and/or purification solvent. For example, Werner, U.S. Pat. No. 2,853,485, issued Sept. 23, 1958, discloses that N-methyl-2-pyrrolidone is a non-reactive solvent for carbohydrates. The examples in Werner show the use of N-methyl-2- pyrrolidone in the conversion of carbohydrates to carbohydrate esters, ethers, and amines. There is no disclosure in Werner regarding the use of N-methyl-2-pyrrolidone in the formation of glycosides or its miscibility with lipophilic alcohols. A more complete listing of uses of N-methyl-2-pyrrolidone is found in M-Pyrol® N-Methyl-2-Pyrrolidone Handbook published by GAF Corporation Chemical Division, 140 West 51st Street, New York, N.Y. 10020.

SUMMARY OF THE INVENTION

The object of this invention is to provide an improved process for preparing medium and long-chain alkyl glycosides. A more particular object is to provide a process for directly and rapidly reacting saccharides and medium and long-chain alcohols without the formation of intermediate compounds and without constraints on the physical form of the saccharide, on the rate of by-product removal, or on the molar ratio of alcohol to saccharide.

We have discovered a process for preparing medium and long-chain alkyl glycosides which comprises reacting a saccharide selected from the group consisting of unsubstituted saccharides, short-chain alkyl glycosides, and mixtures thereof with a monohydric alcohol selected from the group consisting of medium-chain alcohols, long-chain alcohols, and mixtures thereof at a temperature of about 80° to 140° C. in the presence of at least 1 mole N-methyl-2-pyrrolidone per mole saccharide unit.

This process offers many advantages over previously employed processes. First of all, no intermediate reactants are necessarily employed. Therefore, no intermediate products are necessarily produced and there is no necessity of separating intermediate reactants and products from the final product. Secondly, non-crystalline forms of saccharides can be used. Thirdly, the removal of by-products immediately upon formation, although desirable, is not required. Fourthly, the molar ratio of alcohol to saccharide is not critical. And fifthly, the process proceeds relatively quickly.

Unless otherwise indicated, temperatures are expressed in units of degrees Celsius, pressures in millimeters mercury, masses in grams, and percentages are computed based on weight.

DETAILED DESCRIPTION OF THE INVENTION

A. N-Methyl-2-Pyrrolidone

This invention is a process for preparing medium and long-chain alkyl glycosides by reacting a saccharide and a monohydric alcohol in the presence of N-methyl-2-pyrrolidone. The N-methyl-2-pyrrolidone favors the rate of the desired saccharide-alcohol reaction over the competing and undesired saccharide-polymerization reaction. Depending upon the particular saccharide and alcohol chosen, N-methyl-2-pyrrolidone can make the difference between virtually all of the saccharide reacting with the alcohol or, instead, self-polymerizing. The exact role played by the N-methyl-2-pyrrolidone is not known with certainty. It is believed, however, that at least part of its effect is due to the fact that it increases the miscibility of the saccharide and the alcohol and thereby reduces the mass transfer limitations on the rate of their reaction. It is also believed that N-methyl-2-pyrrolidone exhibits some catalytic activity in the reaction.

The N-methyl-2-pyrrolidone is employed in a quantity sufficient to prevent the formation of visually-perceptible distinct phases of the saccharide and the alcohol. This quantity is generally at least 1 mole N-methyl- 2-pyrrolidone per mole saccharide unit. Quantities less than about 1 mole are undesirable since they are not as effective in favoring the saccharide-alcohol reaction. On the other hand, quantities greater than about 25 moles, although operative, are impractical because of the need to later remove excessive amounts of N-methyl-2-pyrrolidone from the products. Other things being equal, greater quantities of N-methyl-2-pyrrolidone are employed when the saccharide and the alcohol are less miscible with one another. It is preferable to employ about 2 to 20, and more preferably about 5 to 15 moles N-methyl-2-pyrrolidone per mole saccharide unit.

When exposed to water at elevated temperatures under acidic conditions, N-methyl-2-pyrrolidone has a tendency to hydrolyze to an open-ringed amino acid which, in turn, forms a salt with the free hydrogen ions. Accordingly, when the process of this invention is carried out in the presence of water and an acid catalyst, the hydrolysis of the N-methyl-2-pyrrolidone places a constraint on the temperatures employed. This constraint on temperature is discussed in more detail below.

B. Saccharides

Unsubstituted saccharides and short-chain alkyl glycosides (i.e., methyl, ethyl, and propyl glycosides) are suitable for use in this process. Longer-chain alkyl glycosides can be used, but the resulting increase in the saccharide-alcohol reaction rate when N-methyl-2-pyrrolidone is used is generally insufficient to justify the expense. Mixtures of unsubstituted saccharides and short-chain alkyl glycosidss, as well as mixtures thereof with longer-chain alkyl glycosides, are also suitable for use in this process.

The identity of the individual monosaccharide units is not especially critical to this process. The choice of monosaccharide unit is primarily dependent upon availability and, to some extent, on stability under the reaction conditions. For example, 5 and 6 carbon saccharide units (i.e., pentoses and hexoses) are generally employed because of their ready availability and stability. Of the pentoses and hexoses, the aldoses (e.g., ribose and glucose) are preferred over the ketoses (e.g., ribulose and fructose) because they are less prone to degradation. The preferred saccharide unit is glucose considering its low cost and ready availability from starch.

The number of saccharide units in the chain (also expressed as D.P.) is more important to the process. Although polysaccharides such as starch and cellulose are suitable, their extreme hydrophilicity requires additional quantities of N-methyl-2-pyrrolidone. It is often simpler and more economical to first obtain a saccharide having a lower D.P. so that a smaller quantity of N-methyl-2-pyrrolidone is required. In general, it is preferred that at least 50 percent of the saccharide have a D.P. of 3 or less. Commonly available corn syrups having dextrose equivalents in the range of 15 to 95 are especially useful sources of such saccharides. The more preferred saccharide for use in the process consists essentially of monosaccharides. The monosaccharides are less hydrophilic and their increased uniformity results in a greater uniformity in the reaction product.

The saccharide may be employed in any physical form, e.g., crystalline solid, amorphous solid, liquid, or solution. Although crystalline solids are suitable and it is well-known that crystalline glucose in its alpha form is a readily available article of commerce, crystalline forms of saccharides are rarely used because they are generally more expensive than other forms which perform as well. An especially inexpensive physical form for a saccharide is that of an aqueous solution. As mentioned above, corn syrups having dextrose equivalents in the range of 15 to 95 are worthy of special mention because of their relatively low cost. Although not required, it is advantageous to minimize the amount of water in an aqueous solution because of water's role in hydrolyzing N-methyl-2-pyrrolidone.

In brief summary, the most preferred unsubstituted saccharides and short-chain alkyl glycosides include unsubstituted glucose, methyl monoglucoside, ethyl monoglucoside, and propyl monoglucoside.

C. Alcohols

Medium and long-chain monohydric alcohols, and mixtures thereof, are used in this invention to react with the saccharides to produce the medium and long-chain alkyl glycosides. Shorter chain-length alcohols can be reacted with the saccharides, but the problems of immiscibility and low reactivity are less severe when such alcohols are used. The alcohols may be primary or secondary, straight-chain or branched, and saturated or unsaturated. The preferred alcohols are the primary, straight-chain, saturated alcohols. The choice of the alcohol chain length depends, of course, on the product desired. In particular, if a surface-active long-chain alkyl glycoside is desired, the preferred alcohols are the monohydric, primary, straight chain, saturated alcohols having 10 to 18 carbon atoms because their lipophilicity balances the hydrophilicity of the saccharides and results in the greatest surface activity in the long-chain alkyl glycosides. The most preferred alcohols are decanol (also known as decyl alcohol), undecanol (also known as undecyl alcohol), dodecanol (also known as dodecyl alcohol and as lauryl alcohol), tridecanol (also known as tridecyl alcohol) and tetradecanol (also known as tetradecyl alcohol and as myristyl alcohol).

The amount of alcohol relative to the amount of saccharide used in this process is not critical. However, this ratio does have an effect on both the physical properties of the reaction medium and on the distribution of reaction products. In particular, at molar ratios of alcohol to saccharide unit of less than about 1:1, the reaction medium becomes viscous and prone to solidify unless additional quantities of N-methyl-2-pyrrolidone are present. At molar ratios of greater than about 15:1, excessive amounts of unreacted alcohol must be separated from the alkyl glycoside product. It is also known that the molar ratio of alcohol to saccharide has an effect on the relative rates of the saccharide-alcohol reaction and the saccharide-polymerization reaction. The higher ratios favor the former and the lower ratios favor the latter. In general, the molar ratio of alcohol to saccharide unit is about 2:1 to 10:1.

D. Other Process Parameters

The temperature at which this process is conducted is glenerally about 80° to 140° C. Temperatures below about 80° C. are undesirable because the rate of the reaction is prohibitively slow. Temperatures above about 140° C. are generally avoided because excessive amounts of N-methyl-2-pyrrolidone hydrolyze (especially in the presence of acid and water). In addition, undesirable color bodies from the degradation of saccharides form in excessive quantities at temperatures above about 140° C. Reaction temperatures of about 100° to 130° C. are preferred.

The reaction of the saccharide and the alcohol produces water if the saccharide is unsubstituted and an alcohol if the saccharide is a glycoside. These by-products do not have to be removed from the alkyl glycoside product during the reaction, but generally are removed to drive the reaction equilibrium toward the products. An additional incentive to remove by-product water is its deleterious role in hydrolyzing N-methyl-2-pyrrolidone. Conventional removal techniques, such as distillation, extraction, and adsorption, are employed.

The reaction pressure is not critical and subatmospheric, atmospheric, and superatmospheric pressures are all suitable. If it is desired to remove the by-product water and/or alcohol, subatmospheric pressures are advantageously employed. The preferred reaction pressure is about 100 to 800 mm. mercury.

Since the reaction of the saccharide and the alcohol to produce an alkyl glycoside is spontaneous in the thermodynamic sense, it proceeds with or without a catalyst. However, the rate of the reaction is extremely slow without a catalyst. Accordingly, it is greatly preferred that a catalyst be employed. Acid catalysts, including Lewis acids, strong inorganic acids, and strong organic acids, are generally employed. Illustrative Lewis acids are boron trifluoride, tin tetrachloride, and aluminum chloride. Common strong inorganic acids include hydrochloric, hydrofluoric, hydriodic, phosphoric, sulfuric, and sulfonic acids. Strong organic acids include the phosphonic and sulfonic acid derivatives of alkyl, aryl, aralkyl, cyclic, and heterocyclic organic compounds. The strong organic acids are preferred as catalysts because of their relatively low corrosiveness and their compatibility with the saccharide and alcohol reactants. The catalysts are generally used without supports, but can be supported on inert carriers. For example, the strong organic catalysts are sometimes incorporated in resins such as sulphonic phenolformaldehyde, polystyrene, and perfluorinated copolymerics.

The catalyst level may be varied over a broad range with the expected effect on the rate of reaction. At the lower end of the range, catalyst levels less than about 5 meq. catalyst per saccharide unit mole are rarely used because the reaction rate is excessively slow. At the other extreme, catalyst levels greater than about 100 meq. per saccharide unit mole are avoided because, at such high levels, the increase in reaction rate is outweighed by the disadvantage of having to neutralize and/or remove the acid after completion of the reaction. The catalyst level is generally in the range of about 5 to 100 meq. catalyst per saccharide unit mole and is preferably in the range of about 20 to 50 meq. catalyst per saccharide unit mole.

The reaction time varies considerably depending on the amount of N-methyl-2-pyrrolidone, type and level of catalyst, temperatures, etc. Reactions are typically completed within about 2 to 8 hours. The reaction is generally terminated by adding base to neutralize the acid catalyst or by cooling.

The various components in the reaction medium (unreacted saccharide, unreacted alcohol, N-methyl-2-pyrrolidone, alkyl glycosides and by-product water and/or alcohol) are generally separated by conventional methods.

E. Special Embodiments

As discussed above, the choice of saccharide and alcohol to use in this process is determined primarily by the product desired and by economics. Therefore, it is impossible to designate a single pair of reactants as being part of the preferred embodiment of the invention. Nevertheless, there are two combinations of saccharides and alcohols which exemplify the utility of the process because the presence of N-methyl-2-pyrrolidone enables the saccharide-alcohol reaction to proceed essentially to completion whereas the same saccharide and alcohol react negligibly in the absence of N-methyl-2-pyrrolidone.

The first combination of special interest is aqueous glucose and dodecanol. In the absence of N-methyl-2-pyrrolidone, the hydrophilic glucose and the lipophilic dodecanol are immiscible. If exposed to reaction conditions of temperature and catalyst, the glucose self-polymerizes but does not react appreciably with the dodecanol. However, in the presence of N-methyl-2-pyrrolidone, dodecyl glucoside is produced in near-stoichiometric quantities.

The second combination worthy of special mention is methyl glucoside and dodecanol. Although methyl glucoside is not as hydrophilic as glucose, it is still immiscible and unreactive with dodecanol in the absence of N-methyl-2-pyrrolidone. The addition of N-methyl-2-pyrrolidone effects the conversion of methyl glucoside and dodecanol to dodecyl glucoside in near-stoichiometric quantities.

F. Examples

These examples are illustrative only.

EXAMPLE 1

This example illustrates that methyl glucoside and dodecanol are unreactive in the absence of N-methyl-2-pyrrolidone.

The following were placed into a 500 ml. round-bottom flask; 7.3 g. methyl glucoside (including both alpha and beta forms) (0.14 moles) dissolved in 57.9 g. methanol; 78.3 g. dodecanol (0.42 moles); and 1.00 g. paratoluene sulfonic acid monohydrate (37.5 meq. per mole methyl glucoside). The flask was placed in a rotary evaporator and heated at 120° C. at a pressure of about 140 mm. mercury. Insoluble solid material began to appear within minutes after the reaction was begun. The reaction was terminated after approximately 5 hours by neutralizing the acid catalyst with methanolic potassium hydroxide.

The insoluble material was filtered, washed with Skellysolve B ® solvent, a hydrocarbon solvent boiling in the range of 60° to 70° C., and then dried by heating at 120° C. at a pressure of about 4 mm. mercury. The dry material, which had a mass of 20.15 g., was analyzed by liquid chromatography and was found to contain approximately 88 weight percent methyl polyglucoside. This corresponds to approximately 0.11 moles of glucose units using the following conversion:

$$\text{Moles glucose units} = (20.15\text{ g. insol. mat'l})\left(\frac{0.88\text{ g. polyglucoside}}{1.00\text{ g. insol. mat'l}}\right)\left(\frac{1\text{ mole glucose unit}}{162\text{ g. polyglucoside}}\right) = 0.11$$

Therefore, of the 0.14 moles of methyl glucoside initially present, approximately 0.11 moles (or 79 percent) formed methyl polyglucoside rather than the desired dodecyl glucoside.

The results of this example are presented in Table I.

EXAMPLE 2

This example illustrates that N-methyl-2-pyrrolidone renders methyl glucoside and dodecanol reactively compatible.

The procedure described in Example 1 was repeated except that 78.26 g. N-methyl-2-pyrrolidone (0.79 moles) was also placed in the flask and that no insoluble solid material was formed during the reaction.

After the reaction was terminated, the volatiles were removed by heating at 120° C. at a pressure of about 4 mm. mercury. The solid material was analyzed and the saccharide-derived material was found to be essentially dodecyl glucoside with only traces of methyl polyglucoside.

The results of this example are presented in Table I.

EXAMPLE 3

This example illustrates that glucose and butanol are relatively unreactive in the absence of N-methyl-2-pyrrolidone.

The following were placed into a one-liter three-necked round-bottom flask: 125.87 g. STALEYDEX® corn syrup, a 95 D.E. corn syrup containing 71.5 weight percent solids (0.5 moles glucose); 296.48 g. n-butanol (4.0 moles); and 25 ml. SkellysolveB® solvent. The flask heated at 125 ° C. at a pressure of about 760 mm. mercury until approximately 30 ml. water (of the approximate 36 ml. water present in the syrup) was removed.

At this point, 4.76 g. paratoluene sulfonic acid monohydrate (50 meq. per mole glucose) was added to the flask to initiate the reaction. Insoluble solid material began to appear within minutes after the reaction was begun. The reaction was conducted at 125° C at a pressure of about 760 mm. mercury for about 3 hours until 14 ml. water was removed. The reaction was terminated by neutralizing the acid catalyst with methanolic potassium hydroxide.

The insoluble material was filtered, washed, and dried as described in Example 1. The dry material had a mass of 33.81 g., of which approximately 90 percent was polyglucose. This corresponds to approximately 0.18 moles. Therefore, approximately 36 percent of the initial glucose polymerized.

The results of this example are presented in Table I.

EXAMPLE 4

This example illustrates that N-methyl-2-pyrrolidone renders glucose and butanol reactively compatible.

The procedure described in Example 3 was repeated except as follows: (1) 377.61 g. N-methyl-2-pyrrolidone (3.81 moles) was initially placed into the flask; (2) 45 ml. Skellysolve B® solvent, instead of 25 ml., was initially placed into the flask; (3) no insoluble solid material formed during the reaction; and (4) the reaction was conducted for about 6 hours.

The volatiles were removed as described in Example 2. The solid material was analyzed and the saccharide-derived material was found to be essentially butyl glucoside with only traces of glucose and polyglucosides.

The results of this example are presented in Table I.

EXAMPLE 5

This example illustrates that glucose and dodecanol are unreactive in the absence of N-methyl-2-pyrrolidone.

Initially, 35.24 g. STALEYDEX® 95 corn syrup (0.14 moles) was placed into a 500 ml. round-bottom flask. The flask was placed in a rotary evaporator and heated at 120° C. at a pressure of about 50 mm. mercury for 0.5 hours to remove most of the water present in the syrup.

At this point, 78.26 g. dodecanol (0.42 moles) and 1.00 g. paratoluene sulfonic acid monohydrate (37.5 meq. per mole glucose) were added to the flask to initiate the reaction. Insoluble solid material began to appear within minutes after the reaction was begun. The reaction was conducted at 120° C. at a pressure of about 50 mm. mercury for 6.5 hours to remove most of the water. The reaction was terminated by cooling to room temperature.

The insoluble material was filtered, washed and dried as described in Example 1. The dry material had a mass of 22.54 g., of which approximately 96 percent was polyglucose. This corresponds to approximately 0.13 moles. Therefore, approximately 93 percent of the initial glucose polymerized.

The results of this example are presented in Table I.

EXAMPLE 6

This example illustrates that N-methyl-2-pyrrolidone renders glucose and dodecanol reactively compatible.

The procedure described in Example 5 was repeated except as follows: (1) 156.52 g. N-methyl-2-pyrrolidone (1.58 moles) was initially placed into the flask; (2) no insoluble solid material was formed during the reaction; and (3) after cooling, the reaction mixture was made slightly alkaline by adding methanolic potassium hydroxide.

The volatiles were removed as described in Example 2. The solid material was analyzed and the saccharide-derived material was found to be essentially dodecyl glucoside with only traces of glucose and polyglucosides.

The results of this example, as well as the prior examples, are presented below in Table I.

TABLE I

Effect of N—Methyl-2-Pyrrolidone on Saccharide Polymerization

| Run | Saccharide | Alcohol | Moles Alcohol Per Mole Saccharide Unit | Moles N—Methyl-2-Pyrrolidone Per Mole Saccharide Unit | Percentage of Saccharide Polymerized |
|---|---|---|---|---|---|
| 1 | Methyl glucoside | Dodecanol | 3.0 | 0 | 79 |
| 2 | Methyl glucoside | Dodecanol | 3.0 | 5.6 | 0 |
| 3 | Glucose | Butanol | 8.0 | 0 | 36 |

TABLE I-continued

Effect of N—Methyl-2-Pyrrolidone on Saccharide Polymerization

| Run | Saccharide | Alcohol | Moles Alcohol Per Mole Saccharide Unit | Moles N—Methyl-2-Pyrrolidone Per Mole Saccharide Unit | Percentage of Saccharide Polymerized |
|---|---|---|---|---|---|
| 4 | Glucose | Butanol | 8.0 | 7.6 | 0 |
| 5 | Glucose | Dodecanol | 3.0 | 0 | 96 |
| 6 | Glucose | Dodecanol | 3.0 | 11.3 | 0 |

The above results confirm that reactive compatibility is a function of the relative hydrophilicity of the saccharide and the relative lipophilicity of the alcohol. In run 3, glucose (relatively high hydrophilicity) and butanol (relatively low lipophilicity) were used. In this run, only 36 percent of the saccharide polymerized rather than reacting with the alcohol. In run 5, glucose was used with dodecanol (relatively high lipophilicity) and 96 percent of the saccharide polymerized. Finally, in run 1, methyl glucoside (a less hydrophilic saccharide) was used with dodecanol and 79 percent of the saccharide polymerized.

The above results also show that the addition of N-methyl-2-pyrrolidone can make the difference between virtually all of the saccharide self-polymerizing or, instead, reacting with the alcohol.

We claim:

1. A process for preparing alkyl glycosides having substituent alkyl groups of 4 to 25 carbon atoms, which process comprises reacting a saccharide selected from the group consisting of unsubstituted saccharides and alkyl glycosides having substituent alkyl groups of 1 to 3 carbon atoms with a monohydric alcohol having 4 to 25 carbon atoms at a temperature of about 80° to 140° C. in the presence of about 5 to 100 meq. acid catalyst per mole saccharide unit and in the presence of at least 1 to about 25 moles N-methyl-2-pyrrolidone per mole saccharide unit.

2. The process of claim 1 wherein at least 50 percent of the saccharides have a D.P. of 3 or less.

3. The process of claim 2 wherein the alcohol concentration is about 1 to 15 moles alcohol per mole saccharide unit.

4. The process of claim 3 wherein the saccharide consists essentially of monosaccharides.

5. The process of claim 4 wherein the temperature is about 100° to 130° C.

6. The process of claim 5 wherein the reaction is conducted in the presence of about 2 to 20 moles N-methyl-2-pyrrolidone per mole monosacharide unit.

7. The process of claim 1 wherein the monosaccharide is selected from the group consisting of glucose and alkyl glucosides having substituent alkyl groups of 1 to 3 carbon atoms.

8. The process of claim 7 wherein the reaction is conducted in the presence of about 20 to 50 meq. strong organic acid catalyst per mole monosaccharide unit.

9. The process of claim 8 wherein the monosaccharide comprises an aqueous glucose solution.

10. The process of claim 10 wherein the alcohol comprises a primary, straight-chain, saturated alcohol having 10 to 18 carbon atoms.

11. The process of claim 8 wherein the monosaccharide comprises methyl glucosides and the alcohol comprises a primary, straight-chain, saturated alcohol having 10 to 18 carbon atoms.

* * * * *